United States Patent
Dreyfus et al.

(10) Patent No.: US 10,377,750 B2
(45) Date of Patent: *Aug. 13, 2019

(54) 5-METHYL-1,3,4-OXADIAZOL-2-YL COMPOUNDS

(71) Applicant: Eli Lilly and Company, Indianapolis, IN (US)

(72) Inventors: Nicolas Jacques Francois Dreyfus, Surrey (GB); Peter James Lindsay-Scott, Middlesex (GB); Richard Edmund Rathmell, Hampshire (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/983,269

(22) Filed: May 18, 2018

(65) Prior Publication Data

US 2018/0339984 A1     Nov. 29, 2018

Related U.S. Application Data

(60) Provisional application No. 62/510,776, filed on May 25, 2017.

(51) Int. Cl.
*C07D 417/14* (2006.01)
*A61P 25/28* (2006.01)

(52) U.S. Cl.
CPC ............ *C07D 417/14* (2013.01); *A61P 25/28* (2018.01); *C07B 2200/09* (2013.01); *C07B 2200/13* (2013.01)

(58) Field of Classification Search
CPC ..... C07D 417/14; C07D 271/02; A61K 31/41
USPC ........................................................ 514/326
See application file for complete search history.

(56) References Cited

U.S. PATENT DOCUMENTS

| | | |
|---|---|---|
| 4,921,887 A | 5/1990 | Matsuo et al. |
| 9,120,781 B2 | 9/2015 | Li et al. |
| 10,081,625 B2 | 9/2018 | Dreyfus et al. |
| 2016/0031871 A1 | 2/2016 | Yu et al. |

FOREIGN PATENT DOCUMENTS

| | | |
|---|---|---|
| WO | 2005/014579 A1 | 2/2005 |
| WO | 2014/159234 A1 | 10/2014 |
| WO | 2016/030443 A1 | 3/2016 |
| WO | 2017/106254 A1 | 6/2017 |

OTHER PUBLICATIONS

Pending U.S. Appl. No. 15/874,947, filed Jan. 19, 2018; First named inventor: Nicolas Jacques Francois Dreyfus; Assignee: Eli Lilly and Company.
Bostrom, et al., "Oxadiazoles in Medicinal Chemistry," J. Med. Chem. 2012, 55, 1817-1830.
Bostrom, et al., Supporting Information for: "Oxadiazoles in Medicinal Chemistry," J. Med. Chem. 2012, 55, 1817-1830.
Chen, et al., "Discovery of new acetylcholinesterase and butyrylcholinesterase inhibitors through structure based virtual screening," RSC Adv., 2017, 7, 3429-3438.
Somani, et al., "Oxadiazole: A biologically important heterocycle" Der Pharma Chemica; 2009, 1 (1): 130-140.
Jonas Bostrum, et al., *J. Med. Chem.*, (2012); pp. 1817-1830; vol. 55.
Chemical Abstract No. [1797647-11-0]; Commercial Source-Aurora Fine Chemicals,7929 Silverton Ave. Suite 609, San Diego, CA, 92126; Order No. A35.639.184; entered STN Jul. 9, 2015.
Sarah Forster, 2014, Increased 0-GlcNAc levels correlate with decreased 0-GlcNAcase levels in Alzheimer disease brain.
Sean Smith , Early preclinical results . . . 2016.
NIH Fact Sheet, Progressive Supranuclear Palsy, Feb. 27, 2018.
Alzheimer Association, alz.org Feb. 27, 2018, Latest Treatment for Alzheimer.

*Primary Examiner* — Rita J Desai
(74) *Attorney, Agent, or Firm* — Nelsen L. Lentz

(57) ABSTRACT

The present invention provides a compound of Formula I:

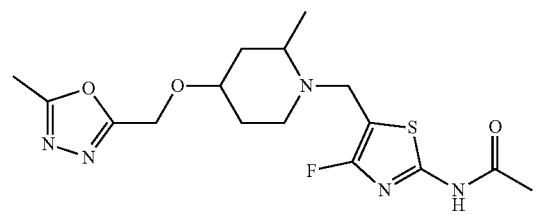

Formula I or a pharmaceutically acceptable salt thereof, and the use of compounds of Formula I for treatment of neurodegenerative diseases and disorders, such as Alzheimer's disease.

13 Claims, No Drawings

5-METHYL-1,3,4-OXADIAZOL-2-YL COMPOUNDS

The present invention relates to novel 5-methyl-1,3,4-oxadiazol-2-yl compounds, to pharmaceutical compositions comprising the compounds, to methods of using the compounds to treat physiological disorders, and to intermediates and processes useful in the synthesis of the compounds.

The present invention is in the field of treatment of Alzheimer's disease, progressive supranuclear palsy (PSP) and other diseases and disorders involving tau-mediated neurodegeneration, known collectively as tauopathies.

Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

The oligomerization of the microtubule-associated protein tau into filamentous structures such as paired helical filaments (PHFs) and straight or twisted filaments, which give rise to neurofibrillary tangles (NFTs) and neuropil threads (NTs), is one of the defining pathological features of Alzheimer's disease and other tauopathies. The number of NFTs in the brains of individuals with Alzheimer's disease has been found to correlate closely with the severity of the disease, suggesting tau has a key role in neuronal dysfunction and neurodegeneration (Nelson et al., J Neuropathol Exp Neurol., 71(5), 362-381(2012)). Tau pathology has been shown to correlate with disease duration in PSP; cases with a more aggressive disease course have a higher tau burden than cases with a slower progression. (Williams et al., Brain, 130, 1566-76 (2007)).

Recent studies (Yuzwa et al., Nat Chem Biol, 4(8), 483-490 (2008)) support the therapeutic potential of O-GlcNAcase (OGA) inhibitors to limit tau hyperphosphorylation and aggregation into pathological tau for the treatment of Alzheimer's disease and related tau-mediated neurodegeneration disorders. Specifically, the OGA inhibitor Thiamet-G has been linked in slowing motor neuron loss in the JNPL3 tau mouse model (Yuzwa et al., Nat Chem Biol, 8, 393-399 (2012)) and to a reduction in tau pathology and dystrophic neurites in the Tg4510 tau mouse model (Graham et al., Neuropharmacology, 79, 307-313 (2014)). Accordingly, OGA inhibitors are recognized as a valid therapeutic approach to reduce the accumulation of hyperphosphorylated, pathological forms of tau.

U.S. Pat. No. 9,120,781 discloses hexahydrobenzooxazole and hexahydrobenzothiazole derivatives which possess OGA inhibitory activity and are further disclosed as useful in treating diseases and disorders related to deficiency or overexpression of OGA, and/or accumulation or deficiency of 2-acetamido-2-deoxy-5β-D-glucopyranoside (O-GlcNAc). In addition, US 2016/0031871 discloses certain glycosidase inhibitors for treating Alzheimer's disease.

OGA inhibitors that are brain penetrant are desired to provide treatments for tau-mediated neurodegeneration disorders, such as Alzheimer's disease and PSP. The present invention provides certain novel compounds that are inhibitors of OGA.

Accordingly, the present invention provides a compound of Formula I:

Formula I

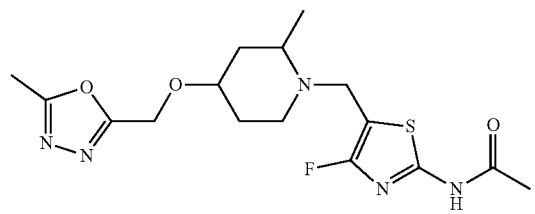

or a pharmaceutically acceptable salt thereof.

In addition, the present invention provides a compound of Formula Ia:

Formula Ia

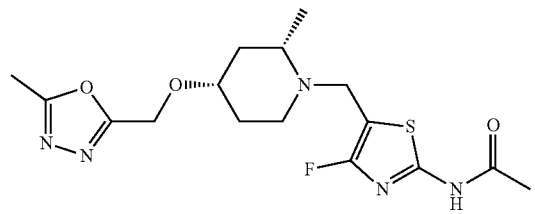

or a pharmaceutically acceptable salt thereof.

The present invention also provides a method of treating Alzheimer's disease in a patient in need of such treatment, comprising administering to the patient an effective amount of a compound of Formulas I or Ia, or a pharmaceutically acceptable salt thereof.

The present invention further provides a method of treating the progression of mild cognitive impairment to Alzheimer's disease in a patient in need of such treatment, comprising administering to the patient an effective amount of a compound of Formulas I or Ia, or a pharmaceutically acceptable salt thereof.

The present invention also provides a method of treating progressive supranuclear palsy in a patient in need of such treatment, comprising administering to the patient an effective amount of a compound of Formulas I or Ia, or a pharmaceutically acceptable salt thereof. The present invention also provides a method of treating tau-mediated neurodegenerative disorders in a patient, comprising administering to a patient in need of such treatment an effective amount of a compound of Formulas I or Ia, or a pharmaceutically acceptable salt thereof.

Furthermore, this invention provides a compound of Formulas I or Ia, or a pharmaceutically acceptable salt thereof for use in therapy, in particular for use in the treatment of Alzheimer's disease or for use in preventing the progression of mild cognitive impairment to Alzheimer's disease. In addition, this invention provides a compound of Formulas I or Ia, or a pharmaceutically acceptable salt thereof for use in the treatment of progressive supranuclear palsy. The invention also provides a compound of Formulas I or Ia, or a pharmaceutically acceptable salt thereof for use in treating tau-mediated neurodegenerative disorders.

Even furthermore, this invention provides the use of a compound of Formulas I or Ia, or a pharmaceutically acceptable salt thereof, for the manufacture of a medicament for the treatment of Alzheimer's disease or for preventing the progression of mild cognitive impairment to Alzheimer's disease. In addition, this invention provides the use of a compound of Formulas I or Ia, or a pharmaceutically acceptable salt thereof, for the manufacture of a medicament for the treatment of progressive supranuclear palsy. The invention also provides the use of a compound of Formulas I or Ia, or a pharmaceutically acceptable salt thereof, for the manufacture of a medicament for treating tau-mediated neurodegenerative disorders.

The invention further provides a pharmaceutical composition, comprising a compound of Formulas I or Ia, or a pharmaceutically acceptable salt thereof, with one or more pharmaceutically acceptable carriers, diluents, or excipients. The invention further provides a process for preparing a pharmaceutical composition, comprising admixing a compound of Formulas I or Ia, or a pharmaceutically acceptable salt thereof, with one or more pharmaceutically acceptable carriers, diluents, or excipients. This invention also encompasses novel intermediates and processes for the synthesis of the compounds of Formulas I and Ia. For example, the invention further provides the following intermediate compound of Formula IIIa:

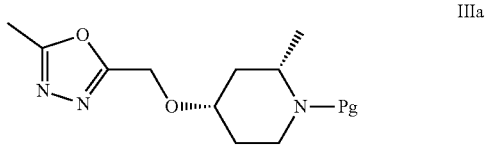

IIIa wherein Pg is a suitable protecting group. Suitable protecting groups include tert-butyl carboxylate and the like.

The invention also provides an intermediate compound of Formula IIa:

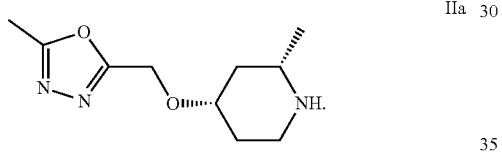

IIa

Mild cognitive impairment has been defined as a potential prodromal phase of dementia associated with Alzheimer's disease based on clinical presentation and on progression of patients exhibiting mild cognitive impairment to Alzheimer's dementia over time. The term "preventing the progression of mild cognitive impairment to Alzheimer's disease" includes restraining, slowing, stopping, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by one skilled in the art by the use of known techniques and by observing results obtained under analogous circumstances. In determining the effective amount for a patient, a number of factors are considered, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are effective at a dosage per day that falls within the range of about 0.1 to about 15 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are formulated as pharmaceutical compositions administered by any route which makes the compound bioavailable, including oral and transdermal routes. Most preferably, such compositions are for oral administration. Such pharmaceutical compositions and processes for preparing same are well known in the art (See, e.g., Remington: The Science and Practice of Pharmacy, L.V. Allen, Editor, $22^{nd}$ Edition, Pharmaceutical Press, 2012).

The compounds of Formulas I and Ia, or pharmaceutically acceptable salts thereof are particularly useful in the treatment methods of the invention, but certain configurations are preferred. The following paragraphs describe such preferred configurations. It will be understood that these preferences are applicable both to the treatment methods and to the compounds of the invention.

Compounds of the present invention include:

Formula Ia

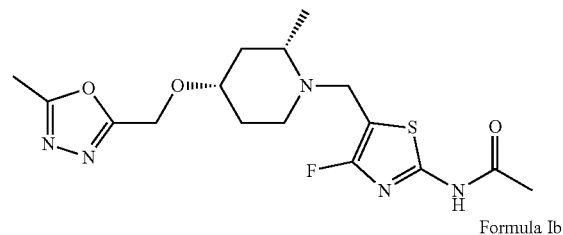

Formula Ib

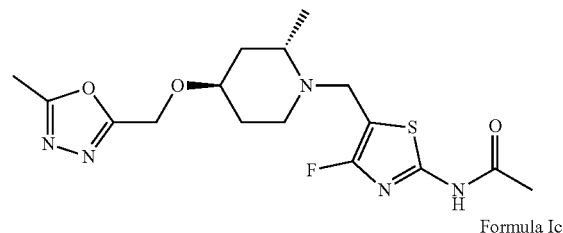

Formula Ic

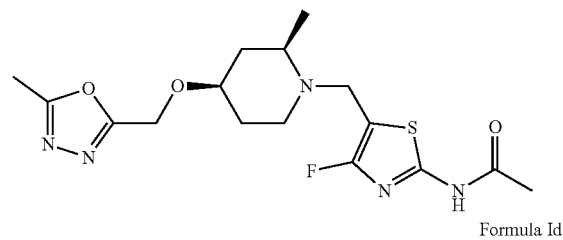

Formula Id

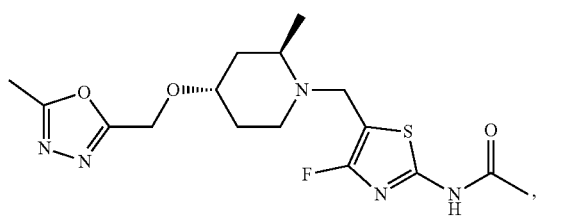

, and pharmaceutically acceptable salts thereof.

The compound of Formula I wherein the methyl and oxygen substituents on the piperidine ring are in the cis or trans configuration, or pharmaceutically acceptable salt thereof, are included within the scope of the invention, with the cis configuration being preferred. For example, one of ordinary skill in the art will appreciate that the methyl at position 2 is in the cis configuration relative to the oxygen at position 4 as shown in Scheme A below:

Scheme A

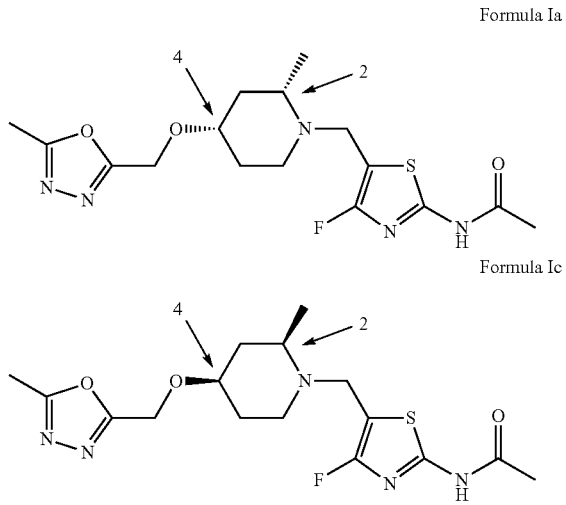

In addition, one of ordinary skill in the art will appreciate that the methyl at position 2 is in the trans configuration relative to the oxygen at position 4 as shown in Scheme B below:

Scheme B

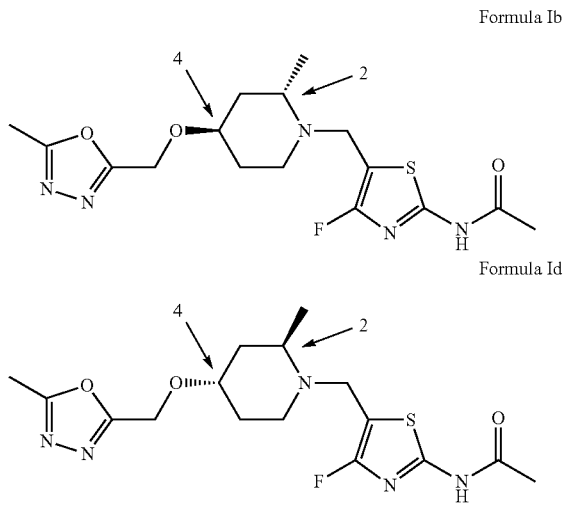

Compounds wherein the chiral center at position 2 of the piperidine ring is in the S-configuration are further preferred. Although the present invention contemplates all individual enantiomers and diastereomers, as well as mixtures of the enantiomers of said compounds, including racemates, the compound with the absolute configuration as set forth below is particularly preferred:

N-[4-fluoro-5-[[(2S,4S)-2-methyl-4-[(5-methyl-1,3,4-oxadiazol-2-yl)methoxy]-1-piperidyl]methyl]thiazol-2-yl]acetamide, and pharmaceutically acceptable salts thereof, with the free base, N-[4-fluoro-5-[[(2S,4S)-2-methyl-4-[(5-methyl-1,3,4-oxadiazol-2-yl)methoxy]-1-piperidyl]methyl]thiazol-2-yl]acetamide, being further preferred.

The crystalline form of N-[4-fluoro-5-[[(2S,4S)-2-methyl-4-[(5-methyl-1,3,4-oxadiazol-2-yl)methoxy]-1-piperidyl]methyl]thiazol-2-yl]acetamide is especially preferred. The crystalline form of N-[4-fluoro-5-[[(2S,4S)-2-methyl-4-[(5-methyl-1,3,4-oxadiazol-2-yl)methoxy]-1-piperidyl]methyl]thiazol-2-yl]acetamide which is characterized by a peak in the X-ray powder diffraction spectrum at diffraction angle 2-theta of 13.5° in combination with one or more peaks selected from the group consisting of 5.8°, 13.0°, 14.3°, 17.5°, 20.4°, 21.4°, and 22.2° with a tolerance for the diffraction angles of 0.2 degrees, is further preferred.

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994).

A pharmaceutically acceptable salt of the compounds of the invention can be formed, for example, by reaction of an appropriate free base of a compound of the invention and an appropriate pharmaceutically acceptable acid in a suitable solvent under standard conditions well known in the art. The formation of such salts is well known and appreciated in the art. See, for example, Gould, P. L., "Salt selection for basic drugs," International Journal of Pharmaceutics, 33: 201-217 (1986); Bastin, R. J., et al. "Salt Selection and Optimization Procedures for Pharmaceutical New Chemical Entities," Organic Process Research and Development, 4: 427-435 (2000); and Berge, S. M., et al., "Pharmaceutical Salts," Journal of Pharmaceutical Sciences, 66: 1-19, (1977).

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention. In addition, one of ordinary skill in the art appreciates that the compounds of Formulas Ia, Ib, Ic, and Id may be prepared by using starting material with the corresponding stereochemical configuration which can be prepared by one of skill in the art. For example, the Schemes below utilize starting materials with the configuration corresponding ultimately to Formula Ia.

Generally, a compound of formula Ia may be prepared from a compound of formula IIa (Scheme 1). More specifically, a compound of formula IIa is reductively alkylated with N-(4-fluoro-5-formylthiazol-2-yl)acetamide in the presence of a suitable reducing agent such as sodium triacetoxyborohydride in a suitable solvent to provide a compound of formula Ia. Suitable solvents include ethyl acetate. N-(4-fluoro-5-formylthiazol-2-yl)acetamide may be prepared by methods known in the chemical arts as well as methods provided in the Preparations and Examples.

A compound of formula IIa may be prepared from a compound of formula IIIa where Pg is a suitable amine protecting group. More specifically, a compound of formula IIIa where Pg is tert-butyl carboxylate (t-BOC) is reacted with an acid such as hydrochloric acid or trifluoroacetic acid in a solvent such as dioxane or dichloromethane to provide a compound of formula IIa. It is understood a compound of formula IIa may be isolated as the free base or as an acid addition salt corresponding to the acid reagent utilized. Suitable amine protecting groups are known in the chemical arts and include t-BOC and Cbz as well as those discussed in T. W. Green, P. G. M. Wuts, "Protective Groups in Organic Synthesis" Wiley-Interscience, New York, 1999.

formula IVa (Scheme 2). More specifically, a compound of formula IVa where Pg is tert-butyl carboxylate is reacted with 2-(chloromethyl)-5-methyl-1,3,4-oxadiazole in the presence of a base such as sodium tert-butoxide to provide a compound of formula IIIa. The reaction is conveniently carried out in a solvent such as acetonitrile or dimethylformamide.

A compound of formula IVa where Pg is tert-butyl carboxylate may be prepared by reducing a compound of formula Va under hydride or enzymatic conditions. More specifically, a compound of formula Va is reacted with a hydride reducing agent such as lithium tri(sec-butyl)borohydride in a solvent such as tetrahydrofuran to provide a compound of formula IVa where Pg is tert-butyl carboxylate. Alternatively, a compound of formula Va is reacted with an enzymatic reducing agent such as ketoreductase in a solvent such as DMSO to provide a compound of formula IV where Pg is tert-butyl carboxylate. A compound of formula Va where Pg is a suitable amine protecting group may be prepared by processes known in the chemical arts including those described in WO 2004/094380 A1.

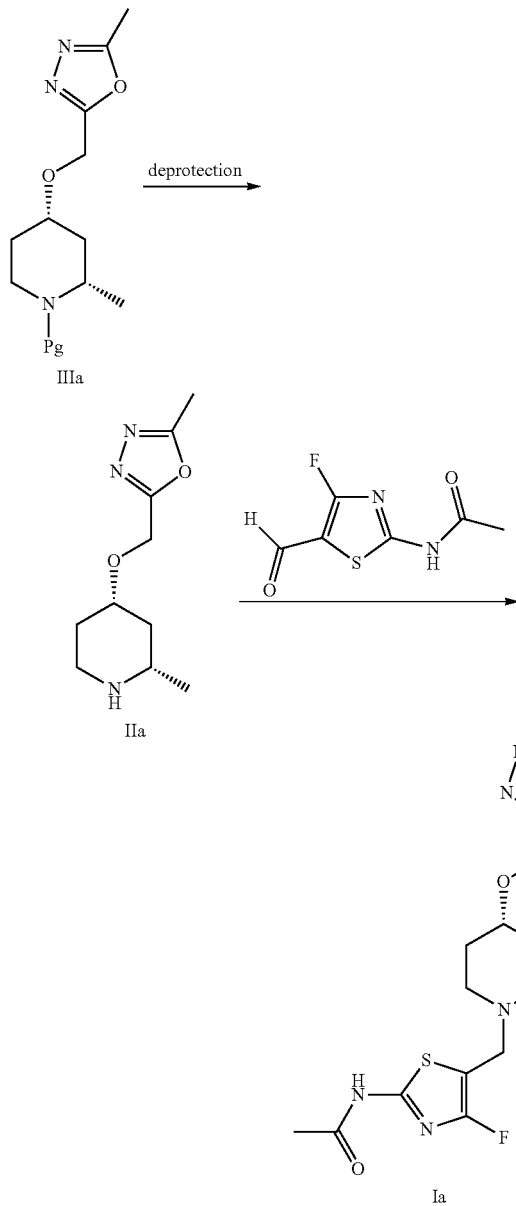

Scheme 1

Scheme 2

A compound of formula IIIa where Pg is a suitable amine protecting group may alternatively be prepared from a compound of formula VIa in a sequence of steps shown in Scheme 3. More specifically, a compound of formula VIa where Pg is tert-butyl carboxylate is reacted with p-toluenesulfonyl chloride in the presence of a base such as diisopropylethylamine to provide a compound of formula IIIa. The reaction is conveniently carried out in a solvent such as acetonitrile. A compound of formula VIa where Pg is tert-butyl carboxylate may be prepared by reacting a compound of formula VIIa with acetohydrazide in the presence of 1,1'-carbonyldiimidazole. The reaction is conveniently carried out in a solvent such as tetrahydrofuran. A compound of formula VIIa where Pg is tert-butyl carboxylate may be prepared by first reacting a compound of formula IVa with 2-chloro-1-morpholino-ethanone and a base such as sodium tert-butoxide in a solvent such as acetonitrile. The resulting morpholino adduct of a compound of formula IVa is then hydrolysed with an aqueous base such as aqueous sodium hydroxide in a solvent such as 2-propanol to provide a compound of formula VIIa where Pg is tert-butyl carboxylate.

A compound of formula IIIa where Pg is a suitable amine protecting group may be prepared from a compound of

Scheme 3

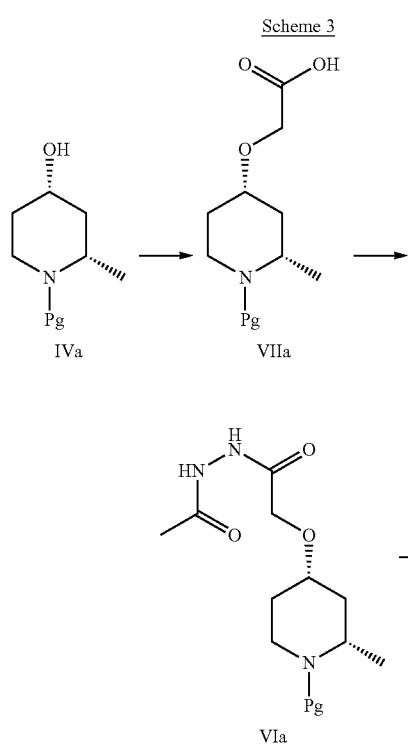

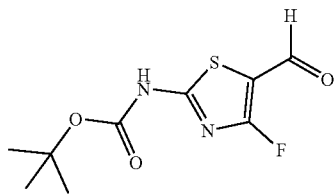 [SMILES: CC(C)(C)OC(=O)Nc1nc(F)c(C=O)s1]

Preparation 1

Synthesis of tert-butyl
N-(4-fluoro-5-formyl-thiazol-2-yl)carbamate

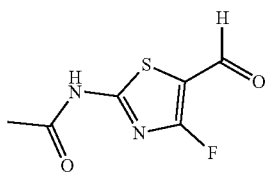

Cesium fluoride (227 g, 1480 mmol) is added to a solution of tert-butyl N-(4-chloro-5-formyl-thiazol-2-yl)carbamate (38.8 g, 148 mmol; for preparation of tert-butyl N-(4-chloro-5-formyl-thiazol-2-yl)carbamate see for example, N. Masuda, et al., *Bioorg Med Chem*, 12, 6171-6182 (2004)) in DMSO (776 mL) at room temperature. The reaction mixture is stirred in a 145° C. heating block with an internal temperature of 133° C. for 48 hours, then the mixture is cooled in an ice-water bath. To the mixture is added saturated aqueous sodium bicarbonate solution (500 mL), brine (500 mL) and ethyl acetate (500 mL). The mixture is stirred at room temperature for 10 minutes, then is filtered through diatomaceous earth, washing with ethyl acetate (500 mL). The filtrate is transferred to a separating funnel and the layers are separated, then the aqueous layer is extracted with ethyl acetate (1 L). The combined organics are washed with brine (1 L), then the brine layer is extracted with ethyl acetate (300 mL). The combined organics are dried over sodium sulfate, filtered and concentrated to give a residue. The residue is passed through a pad of silica gel (330 g) eluting with 5% ethyl acetate in dichloromethane (1.5 L) and the filtrate is concentrated to give a residue (24.2 g, 66% yield assuming 100% purity or 37% yield based on 56% purity measured by $^1$H NMR).

The residue (32.7 g of combined lots, 133 mmol) is dissolved in isopropanol (303 mL), filtered and then is purified by SFC (Supercritical Fluid Chromatography) using an IC column (cellulose polysaccharide derivative: tris (3,5-dichlorophenylcarbamate, 30×250 mm, 5 u)) with 10% IPA (no additive) at 180 mL/minute with 3 mL injections. The product-containing fractions are concentrated to give the title compound (16.1 g, 49%). MS m/z 247.0 (M+H).

Preparation 2

Synthesis
N-(4-fluoro-5-formyl-thiazol-2-yl)acetamide

In a jacketed vessel, zinc bromide (91.9 g, 408 mmol) is added in one portion to a mixture of tert-butyl N-(4-fluoro-5-formyl-thiazol-2-yl)carbamate (33.5 g, 136 mmol) and dichloromethane (503 mL) at room temperature. The reaction mixture is stirred overnight at an internal temperature of 37° C., then the jacket temperature is set to −10° C. and tetrahydrofuran (111 mL) is added dropwise over 15 minutes, maintaining an internal temperature below 6° C. The jacket temperature is then set to −30° C. and pyridine (110 mL, 1360 mmol) is added dropwise over 5 minutes, maintaining an internal temperature below 5° C. The jacket temperature is set to 0° C. and acetic anhydride (116 mL, 1220 mmol) is added dropwise over 5 minutes. The reaction mixture is stirred overnight at an internal temperature of 37° C., then is cooled to room temperature and passed through a short pad of diatomaceous earth, eluting with tetrahydrofuran (500 mL). The filtrate is transferred to a flask and the mixture is concentrated to give a residue, which is concentrated from toluene (50 mL). To the residue is added a solution of citric acid monohydrate (57.2 g, 272 mmol) in water (400 mL) and 2-methyltetrahydrofuran (400 mL) and the mixture is stirred at 40° C. for 5 minutes, then is passed through a short pad of diatomaceous earth, eluting with 2-methyltetrahydrofuran (100 mL). The filtrate is transferred to a separating funnel and the layers are separated. The aqueous layer is extracted with 2-methyltetrahydrofuran (2×250 mL) and the combined organics are diluted with water (500 mL). To the mixture is added solid sodium bicarbonate portionwise over 5 minutes with stirring until gas evolution ceases. The mixture is transferred to a separating funnel and the layers are separated, then the aqueous layer is extracted with 2-methyltetrahydrofuran (200 mL and 100 mL). The combined organics are dried over sodium sulfate, filtered and concentrated to give a residue, which is diluted with 2-methyltetrahydrofuran (100 mL) and the mixture is passed through a short pad of silica gel (250 g), eluting with 2-methyltetrahydrofuran (2.5 L). The filtrate is concentrated to give a residue which is suspended in a 1:1 mixture of dichloromethane and heptane (202 mL). The mixture is stirred at room temperature for 30 minutes and then filtered. The filtered solid is dried under vacuum at 40° C. for 2 hours to give the title compound (18.0 g, 70%). MS m/z 189.0 (M+H).

Alternative Synthesis of N-(4-fluoro-5-formyl-thiazol-2-yl)acetamide

Under an inert atmosphere, dissolve tetramethylammonium fluoride tetrahydrate (100 kg, 605 mol) followed by isopropyl alcohol (453-459 kg) and concentrate under reduced pressure to volume (150-180 L) at temperatures<70° C. Add isopropyl alcohol (453-459 kg) and concentrate under reduce pressure to 150-180 L. Repeat until mixture has a KF<0.2%.

Add dimethylformamide (546-552 kg), heat to 90° C., and concentrate under reduce pressure to 150 L. Add back dimethylformamide (453-459 kg) and concentrate under reduce pressure to 150 L. Repeat until mixture has a residual isopropyl alcohol limit of <60 ppm. Add N-(4-chloro-5-formylthiazol-2-yl)acetamide (15 kg, 73.3 mol) and dimethylformamide (149 kg), and heat to 100° C. for 2-4 hours. Adjust the temperature to 20-25° C. followed by the addition of 2-methyltetrahydrofuran (248 kg). Add 25% wt aqueous ammonium chloride (458 kg) and stir for 30 minutes. Separate the layers and wash the aqueous layer with additional 2-methyltetrahydrofuran (248 kg). Separate the layers and wash the combined organic layers with 25% wt aqueous ammonium chloride (2×458 kg) and stir for 30 minutes.

Add ethyl acetate (180 kg) and heat the reaction mixture to reflux for 1 hour to obtain a clear solution. Concentrate the mixture under reduced pressure at <55° C. to a volume of about 30 L. Add ethyl acetate (54 kg) and concentrate the mixture under reduced pressure at <55° C. to a volume of about 30 L. Stir the mixture at 20-25° C. for 2 hours under nitrogen. Collect the solids by filtration and dry under vacuum at 55-65° C. for 10-12 hours to obtain the title compound (4.5 kg, 82.5% purity).

Preparation 3

Synthesis of tert-butyl (2S,4S)-4-hydroxy-2-methyl-piperidine-1-carboxylate

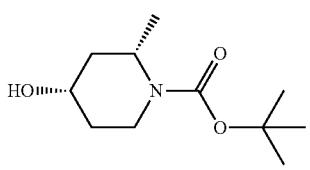

To a flask is added tert-butyl (2S)-2-methyl-4-oxo-piperidine-1-carboxylate (50 g, 234.44 mmol) and tetrahydrofuran (500 mL). The mixture is cooled to −65° C. under an atmosphere of nitrogen and lithium tri(sec-butyl)borohydride (304.77 mL, 304.77 mmol; 1 M in tetrahydrofuran) is added dropwise over 45 minutes, maintaining an internal temperature below −60° C. The reaction mixture is stirred at room temperature for 1 hour, then is cooled to −30° C. To the reaction mixture is added a mixture of water (25.34 mL) and tetrahydrofuran (100.16 mL), maintaining an internal temperature below −20° C. An aqueous solution of hydrogen peroxide (118.88 mL, 1.17 mol, 30 wt/wt %) in water (126.70 mL) is added dropwise over 1 hour, maintaining an internal temperature below 10° C. To the mixture is added aqueous hydrogen chloride solution (46.89 mL, 234.44 mmol, 5 M) and methyl t-butyl ether (1.00 L) and the mixture is warmed to room temperature. The layers are separated and the organic phase is stirred with a solution of sodium metabisulfite (222.84 g, 1.17 mol) in water (500 mL) for 10 minutes at room temperature. The layers are separated and the organic phase is dried over magnesium sulfate and concentrated. The residue is purified by flash chromatography (0-50% methyl t-butyl ether/isohexane, silica gel) and the product-containing fractions are combined and concentrated to give the title compound (40.4 g, 78%). ES/MS (m/e) 238 (M+Na).

Alternative synthesis of tert-butyl (2S,4S)-4-hydroxy-2-methyl-piperidine-1-carboxylate

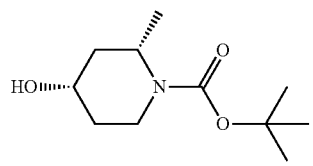

To a glass-lined reactor containing deionized water (460 L), and potassium dihydrogen phosphate (6.5 kg, 0.41 equiv) at 20° C. is charged DMSO (27.4 kg, 1.0 vol) and D-(+)-glucose monohydrate (28.9 kg, 1.25 equiv). The internal temperature is adjusted to 30° C., and the pH of the reaction is adjusted to 6.9 by addition of aqueous sodium hydroxide (8%, 15 L, 0.28 equiv). The reactor is charged with tert-butyl (2S)-2-methyl-4-oxo-piperidine-1-carboxylate (24.9 kg, 1.0 equiv (99.1% ee)), and the mixture is agitated at 30° C. for 15 min. Ketoreductase (KRED-130, 250 g, 1% w/w), glucose dehydrogenase (GDH-101, 250 g, 1% w/w), and NADP sodium salt (63 g, 0.25% w/w) are charged directly to the reaction mixture via an open port. The mixture is maintained at a temperature of 30° C. and pH 7.0±0.2 via addition of 8% aqueous NaHCO$_3$. After stirring for 16.5 h (99.5% conversion), the reaction is charged with Celite™ (12.5 kg, 50 w/w %) and toluene (125 L, 5 vol). After stirring for 30 min at 30° C., the mixture is transferred to another 2000 L reactor via an in-line GAF-filter (4 sock) over the period of 1 h. The mixture is allowed to stand 30 min without agitation, the layers are separated, and the aqueous layer is back-extracted with toluene (2×125 L). The combined organic layers are filtered (in-line GAF-filter), and the toluene mixture is washed with aqueous sodium chloride solution (25%, 125 L, 5 vol) at 25° C. The resulting toluene solution is azeotropically dried (partial vacuum, internal temp<60° C.) to 0.10 w/w % water, and cooled to 20° C. The mixture is filtered out of the reactor via a cartridge filter into clean drums under positive nitrogen pressure. The reaction mixture is then transferred from the drums into a 500 L glass lined vessel and concentrated under vacuum (<60° C.) to a target residual volume of 56 L (2.25 vol). n-Heptane (169 kg, 10 vol) is charged at 40° C., and the mixture is seeded with 25 g of tert-butyl (2S,4S)-4-hydroxy-2-methyl-piperidine-1-carboxylate. The resulting thick slurry is diluted with additional n-heptane (25 L, 1 vol) and cooled to 16° C. over 4 h. The product is isolated via centrifugation, washing with n-heptane (25 L per spin; 4 spins necessary), yielding 20.3 kg (81%; >99.9% ee) after drying for 11 h in a tray dryer at 30° C. ES/MS (m/e) 238 (M+Na).

Preparation 4

Synthesis of 2-[[(2S,4S)-1-tert-butoxycarbonyl-2-methyl-4-piperidyl]oxy]acetic acid

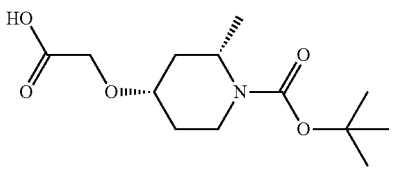 [SMILES: C[C@H]1C[C@@H](OCC(=O)O)CCN1C(=O)OC(C)(C)C]

2-Chloro-1-morpholino-ethanone (59.4 g, 363 mmol) is added to a solution of tert-butyl (2S,4S)-4-hydroxy-2-methyl-piperidine-1-carboxylate (52.1 g, 242 mmol) in acetonitrile (521 mL) at room temperature. The reaction mixture is stirred in an ice-water bath and sodium tert-butoxide (48.0 g, 484 mmol) is added in portions over 10 minutes, maintaining an internal temperature below 15° C. The reaction mixture is stirred at room temperature for 2 hours, then is added over 5 minutes to another flask containing saturated aqueous ammonium chloride solution (250 mL) and water (250 mL) with ice-water bath cooling, maintaining an internal temperature below 15° C. during the addition. The mixture is warmed to room temperature and extracted with methyl tert-butyl ether (2×500 mL), then the combined organics are washed with brine (300 mL). The combined organics are then dried over sodium sulfate, filtered, and concentrated to give a residue, which is combined with 2-propanol (414 mL) and 2M aqueous sodium hydroxide solution (303 mL, 605 mmol) at room temperature. The reaction mixture is stirred in a 47° C. heating block overnight with an internal temperature of 45° C. The reaction mixture is cooled to room temperature and concentrated to remove 2-propanol, then the mixture is diluted with water (50 mL). The mixture is extracted with methyl tert-butyl ether (250 mL), then the aqueous layer is cooled in an ice-water bath and acidified with acetic acid (55.6 mL, 968 mmol). The aqueous mixture is extracted with ethyl acetate (4×250 mL), then the combined organics are dried over sodium sulfate, filtered and concentrated to give a residue, which is concentrated from toluene (3×100 mL) to give the title compound (79.8 g). MS m/z 272.0 (M−H).

Preparation 5

Synthesis of tert-butyl (2S,4S)-4-[2-(2-acetylhydrazino)-2-oxo-ethoxy]-2-methyl-piperidine-1-carboxylate

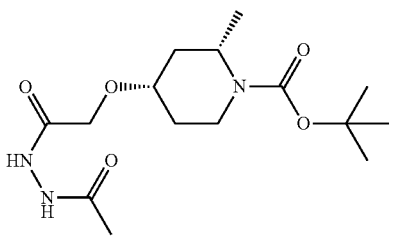 [SMILES: CC(=O)NNC(=O)CO[C@H]1CCN(C(=O)OC(C)(C)C)[C@@H](C)C1]

Tetrahydrofuran (798 mL) is added to a flask containing 2-[[(2S,4S)-1-tert-butoxycarbonyl-2-methyl-4-piperidyl]oxy]acetic acid (79.8 g, 224 mmol, 76.6 mass %) and the mixture is stirred in an ice-water bath with an internal temperature of 5° C. To the mixture is added 1,1'-carbonyldiimidazole (43.5 g, 268 mmol) in one portion and the reaction mixture is stirred at room temperature for 2 hours. An additional portion of 1,1'-carbonyldiimidazole (7.25 g, 44.7 mmol) is added and the reaction mixture is stirred at room temperature for 30 minutes. The reaction mixture is submerged in an ice-water bath and acetohydrazide (21.5 g, 291 mmol) is added in one portion, then the reaction mixture is stirred at room temperature overnight. The reaction mixture is stirred in an ice-water bath and saturated aqueous sodium bicarbonate solution (500 mL) is added over 2 minutes, maintaining an internal temperature below 15° C. The mixture is diluted with water (300 mL) and then is concentrated to remove tetrahydrofuran. The aqueous mixture is extracted with 2-methyltetrahydrofuran (4×500 mL). The combined organics are dried over sodium sulfate, filtered and concentrated to give a residue which is combined with ethyl acetate (200 mL) and heptane (200 mL). The mixture is stirred at room temperature for 30 minutes, then is diluted with heptane (200 mL) and the mixture is stirred vigorously at room temperature for an additional 30 minutes, then is filtered. The filtered solid is dried under vacuum at 40° C. for 2 hours to give the first crop of the title compound (71.5 g). The filtrate is refiltered and the filtered solid is dried under a stream of nitrogen gas at room temperature for 15 minutes to give the second crop of the title compound (1.98 g). The majority of the first crop of product (71.1 g, 216 mmol, unknown purity) and the second crop of product (1.97 g, 5.98 mmol, unknown purity) are combined with tert-butyl methyl ether (731 mL) and the mixture is stirred in a 45° C. heating block for 30 minutes at an internal temperature 40° C., then is cooled to room temperature over 1 hour with stirring and the mixture is filtered. The filtered solid is dried under vacuum at room temperature under a stream of nitrogen gas for 30 minutes to give the title compound (53.7 g). MS m/z 352.0 (M+Na).

Preparation 6

Synthesis of tert-butyl (2S,4S)-2-methyl-4-[(5-methyl-1,3,4-oxadiazol-2-yl)methoxy]piperidine-1-carboxylate

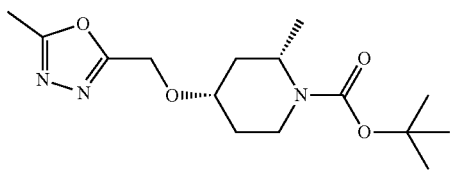 [SMILES: Cc1nnc(CO[C@H]2CCN(C(=O)OC(C)(C)C)[C@@H](C)C2)o1]

To a solution of tert-butyl (2S,4S)-4-hydroxy-2-methyl-piperidine-1-carboxylate (0.5 g, 2 mmol) in N,N-dimethylformamide (5 mL) under nitrogen at room temperature is added portionwise sodium tert-butoxide (0.92 g, 9.28 mmol). The resulting reaction mixture is stirred at room temperature for 40 min. The reaction mixture is cooled to 0° C. and 2-(chloromethyl)-5-methyl-1,3,4-oxadiazole (0.416 g, 3.14 mmol) is added. The resulting solution stirred at room temperature overnight. The reaction mixture is concentrated in vacuo and the residue diluted with water. The mixture is extracted with 3 portions of ethyl acetate. The combined organic extracts are dried over magnesium sulfate, filtered and concentrated under reduced pressure to afford a crude oil. The residue is taken up in dimethyl sulfoxide (to a total volume of 2 ml), and purified by prep-HPLC (Phenomenex Gemini-NX 10 Micron 30*100 mm C-18) (CH₃CN & Water with 10 mM ammonium bicarbonate adjusted to pH 9 with ammonium hydroxide, 15% to 100% CH₃CN over 7 min at 50 ml/min) (1 injection) (204 nm) to afford the title compound (0.028 g, 0.089 mmol, 4%). MS m/z 312.0 (M+H).

Alternative synthesis of tert-butyl (2S,4S)-2-methyl-4-[(5-methyl-1,3,4-oxadiazol-2-yl)methoxy]piperidine-1-carboxylate

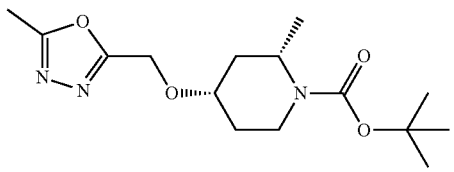 [SMILES: Cc1nnc(CO[C@H]2CCN(C(=O)OC(C)(C)C)[C@@H](C)C2)o1]

To a flask is added tert-butyl (2S,4S)-4-[2-(2-acetylhydrazino)-2-oxo-ethoxy]-2-methyl-piperidine-1-carboxylate (53.7 g, 163 mmol) and acetonitrile (537 mL) and the slurry is stirred at room temperature. To the mixture is added N,N-diisopropylethylamine (114 mL, 652 mmol) in one portion and p-toluenesulfonyl chloride (77.7 g, 408 mmol) in three portions over 5 minutes with water bath cooling. The reaction mixture is stirred at room temperature overnight, then is cooled in an ice-water bath and N',N'-dimethyl-ethane-1,2-diamine (21.8 g, 245 mmol) is added dropwise over 10 minutes, maintaining an internal temperature below 15° C. The reaction mixture is stirred at room temperature for 30 minutes, then is diluted with saturated aqueous citric acid solution (50 mL), ethyl acetate (500 mL) and water (450 mL) at room temperature. The layers are separated and the organic layer is washed with a mixture of saturated aqueous citric acid solution (50 mL) and water (450 mL). The organic layer is washed with saturated aqueous sodium bicarbonate solution (500 mL) and the aqueous layer is then extracted with ethyl acetate (500 mL). The combined organics are dried over sodium sulfate, filtered and concentrated to give a residue, which is passed through a short pad of silica gel (400 g), eluting with 25% ethyl acetate in heptane (2×500 mL fractions) and then with ethyl acetate (5×500 mL fractions). The product-containing fractions are concentrated to give the title compound (53.3 g). MS m/z 312.2 (M+H).

Preparation 7

Synthesis of 5-methyl-5-[[(2S,4S)-2-methyl-4-piperidyl]oxymethyl]-1,3,4-oxadiazole 2,2,2-trifluoroacetic acid

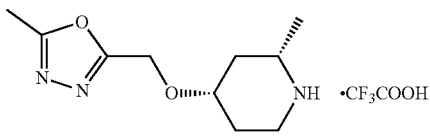

To a solution of tert-butyl (2S,4S)-2-methyl-4-[(5-methyl-1,3,4-oxadiazol-2-yl)methoxy]piperidine-1-carboxylate (0.0275 g, 0.0883 mmol) in dichloromethane (3 mL) under nitrogen is added trifluoroacetic acid (0.035 mL, 0.45 mmol). The mixture is stirred at room temperature overnight. The mixture is concentrated under reduced pressure afford the title compound (0.04 g, 84%). MS m/z 212.0 (M+H).

Preparation 8

Synthesis of 2-methyl-5-[[(2S,4S)-2-methyl-4-piperidyl]oxymethyl]-1,3,4-oxadiazole

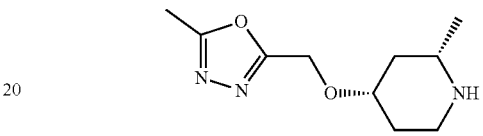

To a flask is added tert-butyl (2S,4S)-2-methyl-4-[(5-methyl-1,3,4-oxadiazol-2-yl)methoxy]piperidine-1-carboxylate (52.9 g, 170 mmol) and dichloromethane (265 mL) at room temperature. The reaction mixture is stirred in an ice-water bath at an internal temperature of 5° C. and trifluoroacetic acid (3500 mmol, 265 mL) is added dropwise over 5 minutes, maintaining an internal temperature below 10° C. The reaction mixture is stirred at room temperature for 15 minutes, then is concentrated to give a residue, which is diluted with water (300 mL) and methyl tert-butyl ether (300 mL). The layers are separated and the aqueous layer is stirred in an ice-water bath and basified with 50% aqueous sodium hydroxide solution (20 mL), maintaining an internal temperature below 10° C. during the addition. The mixture is extracted with dichloromethane (4×300 mL) and the combined organics are dried over sodium sulfate, filtered and concentrated to give the title compound (30.5 g). MS m/z 212.2 (M+H).

EXAMPLE 1

Synthesis of N-[4-fluoro-5-[[(2S,4S)-2-methyl-4-[(5-methyl-1,3,4-oxadiazol-2-yl)methoxy]-1-piperidyl]methyl]thiazol-2-yl]acetamide

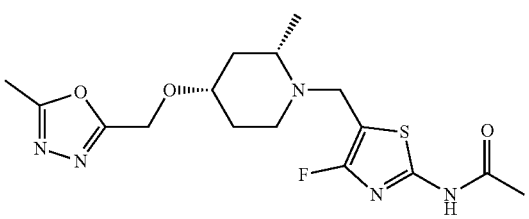 [SMILES: CC(=O)Nc1nc(F)c(CN2CC[C@H](OCc3nnc(C)o3)C[C@@H]2C)s1]

To a solution of 2-methyl-5-[[(2S,4S)-2-methyl-4-piperidyl]oxymethyl]-1,3,4-oxadiazole-2,2,2-trifluoroacetic acid (0.16 g, 0.7 mmol) in ethyl acetate (1 mL) under nitrogen is added N,N-diisopropylethylamine (0.021 mL, 0.12 mmol) and the solution stirred for 5 minutes. N-(4-fluoro-5-formyl-thiazol-2-yl)acetamide (0.04 g, 0.122 mmol) is added and stirred for 5 minutes, sodium triacetoxyborohydride (0.055 g, 0.25 mmol) is added and reaction mixture is warmed to 40° C. and stirred overnight. The mixture is concentrated under reduced pressure to afford a brown solid.

The residue is taken up in dimethyl sulfoxide (to a total volume of 1 ml) and purified by prep-HPLC (Phenomenex Gemini-NX 10 Micron 30*100 mm C-18) (CH₃CN & Water with 10 mM ammonium bicarbonate adjusted to pH 9 with ammonium hydroxide, 15% to 100% CH₃CN over 12 min at 100 ml/min) (1 injection) (271/204 nm) to give title compound (0.007 g, 14%). MS m/z 384.2 (M+H).

Alternative synthesis of crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide

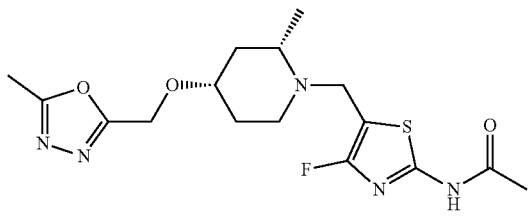 [SMILES: CC(=O)Nc1nc(F)c(CN2CC[C@H](OCc3nnc(C)o3)C[C@@H]2C)s1]

Sodium triacetoxyborohydride (59.1 g, 279 mmol) is added to a mixture of 2-methyl-5-[[(2S,4S)-2-methyl-4-piperidyl]oxymethyl]-1,3,4-oxadiazole (23.3 g, 93.0 mmol), ethyl acetate (438 mL) and N,N-diisopropylethylamine (32.4 mL, 186 mmol) at room temperature. The reaction mixture is stirred in a 31° C. heating block for 15 minutes with an internal temperature of 30° C., then N-(4-fluoro-5-formyl-thiazol-2-yl)acetamide (17.5 g, 93.0 mmol) is added portionwise over 5 minutes. The reaction mixture is stirred in a 31° C. heating block overnight with an internal temperature of 30° C., then is cooled in an ice-water bath to an internal temperature of 5° C. To the mixture is added 2M aqueous hydrochloric acid solution (140 mL) over 15 minutes, maintaining an internal temperature below 10° C. The mixture is stirred at room temperature for 15 minutes, then is diluted with water (50 mL) and ethyl acetate (20 mL) and the layers are separated. The organic layer is extracted with a mixture of 2M aqueous hydrochloric acid solution (35 mL) in water (100 mL). The combined aqueous layers are stirred in an ice-water bath and 50% aqueous sodium hydroxide solution (19.5 mL) is added dropwise over 10 minutes, maintaining an internal temperature below 10° C. The mixture is diluted with saturated aqueous sodium bicarbonate solution (50 mL), then is extracted with 2-methyltetrahydrofuran (3×200 mL). The combined organics are dried over sodium sulfate, filtered and concentrated to give a residue, which is purified by flash chromatography, eluting with 0-15% 2-propanol in dichloromethane. The product-containing fractions are concentrated to give a residue, which is concentrated from heptane (100 mL). The concentrated material is combined with 40% ethyl acetate in heptane (457 mL) and the mixture is stirred in a 50° C. heating block for 1 hour, then is cooled to room temperature and filtered. The filtered solid is dried under vacuum at 40° C. for 1 hour to give a first crop of product (22.9 g). The filtrate is concentrated to give a residue, which is combined with 40% ethyl acetate in heptane (50 mL) and the mixture is stirred in a 50° C. heating block for 30 minutes, then is cooled to room temperature and filtered. The filtered solid is combined with 50% ethyl acetate in heptane (33 mL) and the mixture is stirred in a 50° C. heating block for 1 hour, then is cooled to room temperature and filtered. The filtered solid is dried under vacuum at 40° C. for 1 hour to give a second crop of product (2.50 g).

A combination of lots including the first and second crops of product (29.3 g, 76.4 mmol) is combined with ethyl acetate (117 mL) and heptane (117 mL) at room temperature. The mixture is stirred in a 51° C. heating block for 30 minutes at an internal temperature of 50° C., then is cooled to room temperature and filtered. The filtered solid is dried overnight at 40° C. under vacuum to give the title compound (26.7 g) as a crystalline solid. MS m/z 384.0 (M+H), $[\alpha]_D^{20}=+39°$ (C=0.2, methanol).

X-Ray Powder Diffraction (XRPD) of crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide Crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide (218 mg) is dissolved in 1.25 mL of methanol at 60° C. for 5 minutes. The solution is cooled to ambient temperature with stirring for 20 minutes. The resulting solid is isolated by vacuum filtration. The final solid product is 163 mg or 75% yield.

The XRD patterns of crystalline solids are obtained on a Bruker D4 Endeavor X-ray powder diffractometer, equipped with a CuKa source ($\lambda$=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 38—National Formulary 35 Chapter <941> Characterization of crystalline and partially crystalline solids by X-ray powder diffraction (XRPD) Official May 1, 2015. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of +0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, were adjusted based on NIST 675 standard peaks at 8.85 and 26.77 degrees 2-theta.

Thus, crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide is characterized by an XRD pattern using CuKa radiation as having diffraction peaks (2-theta values) as described in Table 1. More specifically, the pattern preferably contains a peak at 13.50 in combination with one or more peaks selected from the group consisting of 5.8°, 13.0°, 14.3°, 17.5°, 20.4°, 21.4°, and 22.2° with a tolerance for the diffraction angles of 0.2 degrees.

TABLE 1

X-ray powder diffraction peaks of crystalline N-[4-fluoro-5-[[(2S,4S)-2-methyl-4-[(5-methyl-1,3,4-oxadiazol-2-yl)methoxy]-1-piperidyl]methyl]thiazol-2-yl]acetamide.

| Peak | Angle (2-Theta °) | Intensity (%) |
|---|---|---|
| 1 | 5.8 | 78 |
| 2 | 9.2 | 18 |
| 3 | 11.7 | 24 |
| 4 | 13.0 | 34 |
| 5 | 13.5 | 100 |
| 6 | 14.3 | 39 |
| 7 | 17.5 | 50 |
| 8 | 18.3 | 30 |
| 9 | 19.7 | 11 |
| 10 | 20.1 | 14 |
| 11 | 20.4 | 43 |
| 12 | 20.7 | 17 |
| 13 | 21.4 | 37 |
| 14 | 22.0 | 17 |
| 15 | 22.2 | 39 |
| 16 | 23.1 | 12 |
| 17 | 23.8 | 16 |
| 18 | 23.9 | 25 |
| 19 | 24.9 | 19 |
| 20 | 25.2 | 30 |
| 21 | 28.7 | 10 |
| 22 | 37.0 | 11 |

In Vitro Human OGA Enzyme Assay

Generation of OGA Proteins

The nucleotide sequence encoding full-length human O-GlcNAc-β-N-acetylglucosaminidase (NM_012215) is inserted into pFastBac1 (Invitrogen) vector with an N-terminal poly-histidine (HIS) tag. Baculovirus generation is carried out according to the Bac-to-Bac Baculovirus Expression system (Invitrogen) protocol. Sf9 cells are infected at $1.5 \times 10^6$ cells/mL using 10 mL of P1 virus per Liter of culture and incubated at 28° C. for 48 hrs. Cells are spun down, rinsed with PBS and the pellets stored at −80° C. The above OGA protein (His-OGA) is purified as follows: 4 L of cells are lysed in 200 mL of buffer containing 50 mM Tris, pH 8.0, 300 mM NaCl, 10% glycerol, 10 mM Imidazol, 1 mM Dithiothreitol (DTT), 0.1% Triton™ X-100, 4 tablets of protease inhibitors (complete EDTA-Free, Roche) for 45 min at 4° C. This cell lysate is then spun for 40 min at 16500 rpm at 4° C., and supernatant incubated with 6 mL of Ni-NTA resin (nickel-nitrilotriacetic acid) for 2 hours at 4° C.

Resin is then packed onto column and washed with 50 mM Tris, pH 8.0, 300 mM NaCl, 10% glycerol, 10 mM Imidazole, 0.1% Triton™ X-100, 1 mM DTT, followed by 50 mM Tris, pH 8.0, 150 mM NaCl, 10 mM Imidazol, 10% glycerol, 1 mM DTT. The proteins are eluted with 50 mM Tris, pH 8.0, 150 mM NaCl, 300 mM Imidazole, 10% glycerol, 1 mM DTT. Pooled His-OGA containing fractions are concentrated to 6 ml and loaded onto Superdex75 (16/60). The protein is eluted with 50 mM Tris, pH 8.0, 150 mM NaCl, 10% glycerol, 2 mM DTT. Fractions containing His-OGA are pooled and protein concentration measured with BCA (Bradford Colorimetric Assay).

OGA Enzyme Assay

The OGA enzyme catalyses the removal of O-GlcNAc from nucleocytoplasmic proteins. To measure this activity Fluorescein di-N-acetyl-β-N-acetyl-D-glucosaminide (FD-GlcNAc, Kim, Eun Ju; Kang, Dae Ook; Love, Dona C.; Hanover, John A. Carbohydrate Research (2006), 341(8), 971-982) is used as a substrate at a final concentration of 10 μM (in the 96 well assay format) or 6.7 μM (in the 384 well assay format). This fluorogenic substrate becomes fluorescent upon cleavage by OGA, so that the enzyme activity can be measured by the increase in fluorescence detected at 535 nm (excitation at 485 nm).

The assay buffer is prepared to give a final concentration of 50 mM $H_2NaPO_3$—$HNa_2PO_3$, 0.01% bovine serum albumin and 0.01% Triton™ X-100 in water, at pH 7. The final enzyme concentration is 3 nM (in the 96 well assay format) or 3.24 nM (in the 384 well assay format). Both assay formats yield essentially equivalent results.

Compounds to be tested are diluted in pure dimethyl sulfoxide (DMSO) using ten point concentration response curves. Maximal compound concentration in the reaction mixture is 30 μM. Compounds at the appropriate concentration are pre-incubated with OGA enzyme for 30 minutes before the reaction is started by the addition of substrate. Reactions are allowed to proceed for 60 minutes at room temperature. Then, without stopping the reaction, fluorescence is read. $IC_{50}$ values are calculated by plotting the normalized data vs. log of the compound and fitting the data using a four parameter logistic equation.

The compound of Example 1 was tested essentially as described above and exhibited an $IC_{50}$ of 2.13 nM±0.89 (n=5). This result demonstrates that the compound of Example 1 inhibits OGA enzyme activity in vitro.

Whole Cell Assay for Measuring the Inhibition of OGA Enzyme Activity

Cell Plating:

Utilizing standard conditions known in the art, TRex-293 cells modified for inducible expression of the P301S-1N4R form of the microtubule associated protein tau are generated and maintained in growth media, consisting of DMEM High Glucose (Sigma#D5796), supplemented with 10% Tetracyclin-free Fetal Bovine Serum (FBS, Sigma F2442), 20 mM HEPES, 5 μg/mL Blasticidin (Life Technologies#A11139-03) and 200 μg/mL Zeocin (Life Technologies#R250-01). For the experiments, cells are plated in growth media at 10,000-14,000 cells per well in a Corning Biocoat (356663) 384 well plate coated with poly-D-Lysine, and incubated 20-24 h in a cell incubator at 37° C./5% $CO_2$. Experiments are performed without inducing Tau expression.

Compound Treatment:

Compounds to be tested are serially diluted ⅓ in pure DMSO using ten point concentration response curves and further diluted in growth media. 20-24 h after plating, cells are treated with test compound in growth media; maximal compound concentration is 15 μM (0.15% DMSO). The maximum inhibition is defined by replicate measurements of 15 uM Thiamet G and the minimum inhibition is defined by replicate measurements of 0.15% DMSO treatment. The cells are returned to the incubator at 37° C./5% $CO_2$ for 20-24 hours. Compounds are tested in duplicates within each plate.

Immunostaining:

After 20-24 hours of compound treatment, the media is removed from the assay plate and 25 μL of 3.7% Formaldehyde solution (Sigma #F1635) in DPBS (Sigma #D8537; Dulbecco's phosphate buffered saline) is added to each well and incubated for 30 minutes. The cells are then washed once with DPBS and then permeabilized with 0.1% Triton™ X-100 (Sigma#T9284). After 30 minutes, cells are washed twice with DPBS and then blocking solution (1% BSA/

DPBS/0.1% Triton™ X-100) is added to each well and incubated for 60 minutes. The blocking solution is removed and a 0.40-0.33 μg/mL solution of O-GlcNAc Protein antibody (RL2 clone, Thermo, MA1072) in blocking solution is added to the cells and allowed to sit overnight at 2-8° C. The next day, the cells are washed twice with DPBS and the secondary antibody, Alexa Fluor 488 goat anti-mouse IgG (Life Technologies #A11001) at 2 ug/mL in DPBS is added to each well and allowed to sit at room temperature for 90 min. The secondary antibody is removed, cells washed twice with DPBS and a solution of DAPI (Sigma #D9564; 4',6-diamidino-2-phenylindole, dilactate) and RNase (Sigma, R6513) in DPBS at a concentration of 1 and 50 ug/mL, respectively, is added to each well. The plate is sealed, incubated for one hour and analyzed on an Acumen eX3 hci (TTP Labtech). All the incubations and washing steps described above are done at room temperature, except for the primary antibody.

Analysis and Results:

The plates are analyzed on an Acumen eX3 instrument using a 488 and 405 nm excitation lasers and two emission filters FL2 (500-530 nm) and FL1 (420-490 nm). The FL2 filter is the signal corresponding to the O-GlcNAc Protein antibody (RL2 clone) and the FL1 filter is the signal corresponding to the cell nuclei (DAPI). The ratio Total FL2/Total FL1 (Total fluorescence of each well without object or population selection) is used for data analysis. The data are normalized to a maximum inhibition as referenced by a 15 μM treatment of Thiamet G and a minimum inhibition as achieved by a 0.15% DMSO treatment. The data are fitted with a non-linear curve fitting application (4-parameters logistic equation) and $IC_{50}$ values are calculated and reported.

The compound of Example 1 was tested essentially as described above and exhibited an $IC_{50}$ of 22.6 nM±7.3 (n=3). This result demonstrates that the compound of Example 1 inhibits OGA enzyme activity in a cellular assay.

We claim:

1. A compound of the formula:

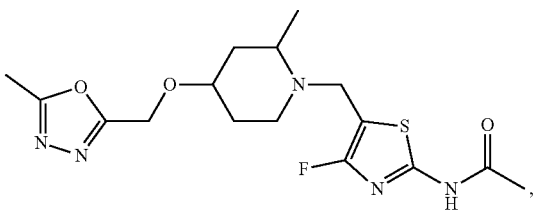

or a pharmaceutically acceptable salt thereof.

2. The compound or salt according to claim 1 wherein the methyl at position 2 is in the cis configuration relative to the oxygen at position 4 on the piperidine ring:

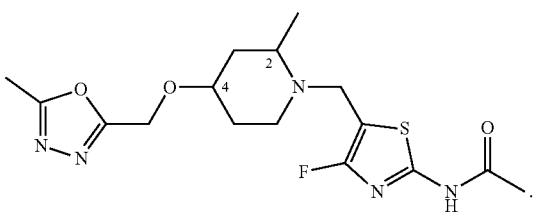

3. The compound or salt according to claim 1 wherein the methyl at position 2 is in the trans configuration relative to the oxygen at position 4 on the piperidine ring:

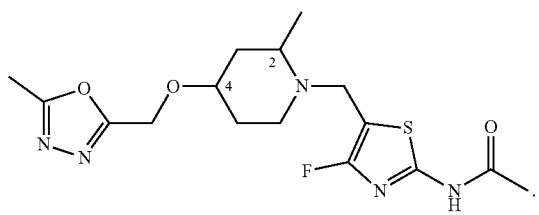 [SMILES: CC(=O)Nc1nc(F)c(CN2CCC(OCc3nnc(C)o3)CC2C)s1]

4. The compound or salt according to claim 2 wherein the compound is N-[4-fluoro-5-[[(2S,4S)-2-methyl-4-[(5-methyl-1,3,4-oxadiazol-2-yl)methoxy]-1-piperidyl]methyl]thiazol-2-yl]acetamide.

5. The compound according to claim 4 which is N-[4-fluoro-5-[[(2S,4S)-2-methyl-4-[(5-methyl-1,3,4-oxadiazol-2-yl)methoxy]-1-piperidyl]methyl]thiazol-2-yl]acetamide.

6. The compound according to claim 5 wherein the compound is crystalline.

7. The compound according to claim 6 which is characterized by a peak in the X-ray powder diffraction spectrum at diffraction angle 2-theta of 13.5° in combination with one or more peaks selected from the group consisting of 5.8°, 13.0°, 14.3°, 17.5°, 20.4°, 21.4°, and 22.2° with a tolerance for the diffraction angles of 0.2 degrees.

8. A pharmaceutical composition, comprising a compound or a pharmaceutically acceptable salt thereof according to claim 1 with one or more pharmaceutically acceptable carriers, diluents, or excipients.

9. A pharmaceutical composition, comprising a compound or a pharmaceutically acceptable salt thereof according to claim 4 with one or more pharmaceutically acceptable carriers, diluents, or excipients.

10. A process for preparing a pharmaceutical composition, comprising admixing a compound or a pharmaceutically acceptable salt thereof according to claim 1 with one or more pharmaceutically acceptable carriers, diluents, or excipients.

11. A process for preparing a pharmaceutical composition, comprising admixing a compound or a pharmaceutically acceptable salt thereof according to claim 4 with one or more pharmaceutically acceptable carriers, diluents, or excipients.

12. A pharmaceutical composition, comprising a compound or a pharmaceutically acceptable salt thereof according to claim 2 with one or more pharmaceutically acceptable carriers, diluents, or excipients.

13. A pharmaceutical composition, comprising a compound according to claim 5 with one or more pharmaceutically acceptable carriers, diluents, or excipients.

* * * * *